(12) United States Patent
Saenz Villalobos et al.

(10) Patent No.: US 11,857,159 B2
(45) Date of Patent: Jan. 2, 2024

(54) ENDOSCOPE LUMEN ACCESSORY AND METHODS OF USE

(71) Applicant: Boston Scientific Scimed, Inc., Maple Grove, MN (US)

(72) Inventors: Gonzalo Jose Saenz Villalobos, Alajuela (CR); Yeison Calvo, Alajuela (CR); Diana Catalina Rodriguez Forero, Galway (IE); Juan Pablo Ortiz Garcia, Alajuela (CR); Andres Rodriguez Herrera, Alajuela (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 186 days.

(21) Appl. No.: 17/177,398

(22) Filed: Feb. 17, 2021

(65) Prior Publication Data

US 2021/0251474 A1  Aug. 19, 2021

Related U.S. Application Data

(60) Provisional application No. 62/977,889, filed on Feb. 18, 2020.

(51) Int. Cl.
*A61B 1/00* (2006.01)
*A61B 1/018* (2006.01)

(52) U.S. Cl.
CPC ........ *A61B 1/00137* (2013.01); *A61B 1/0014* (2013.01); *A61B 1/00097* (2022.02); *A61B 1/00098* (2013.01); *A61B 1/00101* (2013.01); *A61B 1/018* (2013.01)

(58) Field of Classification Search
CPC .............. A61B 1/00137; A61B 1/0014; A61B 1/00098; A61B 1/00101
See application file for complete search history.

(56) References Cited

U.S. PATENT DOCUMENTS

| | | | | |
|---|---|---|---|---|
| 5,386,817 A | * | 2/1995 | Jones | A61B 1/00135 600/125 |
| 6,352,503 B1 | * | 3/2002 | Matsui | A61B 1/00154 600/106 |
| 6,761,685 B2 | * | 7/2004 | Adams | A61B 1/00073 600/146 |
| 8,277,373 B2 | * | 10/2012 | Maahs | A61B 1/00179 600/113 |

(Continued)

OTHER PUBLICATIONS

Matthes et al. "Feasibility of endoscopic transgastric distal pancreatectomy in a porcine animal model." Gastrointestinal Endoscopy, 66(4), pp. 762-766, 2007.

(Continued)

*Primary Examiner* — Matthew J Kasztejna
(74) *Attorney, Agent, or Firm* — Bookoff McAndrews, PLLC

(57) ABSTRACT

An accessory device for an endoscope includes a cap attached to a shaft of the endoscope, the cap extending along a first axis, a first tip coupled to the cap and movable relative to the cap between a deployed configuration and a non-deployed configuration, and a first shaft defining a lumen and extending proximally from the first tip. In the deployed configuration, the first tip extends along a second axis that is offset from the first axis, and in the non-deployed configuration, the first tip extends along a third axis that is offset from the first axis.

20 Claims, 5 Drawing Sheets

(56) References Cited

U.S. PATENT DOCUMENTS

| | | |
|---|---|---|
| 8,684,912 B2 * | 4/2014 | Deviere .............. A61B 1/00087 600/129 |
| 9,596,980 B2 | 3/2017 | Marescaux et al. |
| 11,369,399 B2 * | 6/2022 | Bagwell ................. A61B 17/30 |
| 2004/0015050 A1 * | 1/2004 | Goto .................. A61B 18/1492 600/104 |
| 2005/0096502 A1 * | 5/2005 | Khalili ................... A61B 34/72 600/129 |
| 2005/0234296 A1 * | 10/2005 | Saadat ................. A61B 1/0008 600/173 |
| 2005/0234297 A1 * | 10/2005 | Devierre ............ A61B 1/00087 600/129 |
| 2007/0167679 A1 * | 7/2007 | Miyamoto ........... A61B 1/0055 600/129 |
| 2008/0071289 A1 * | 3/2008 | Cooper .................. A61B 34/70 901/14 |
| 2010/0036198 A1 * | 2/2010 | Tacchino ............... A61B 17/29 600/106 |

OTHER PUBLICATIONS

Willingham et al."Natural orifice versus conventional laparoscopic distal pancreatectomy in a porcine model: a randomized, controlled trial." Gastrointestinal Endoscopy, 70(4), pp. 740-747, 2009.

Allemann et al. "NOTES new frontier: Natural orifice approach to retroperitoneal disease." World Journal of Gastrointestinal Surgery, 2(5), pp. 157-164, 2010.

* cited by examiner

ENDOSCOPE LUMEN ACCESSORY AND METHODS OF USE

CROSS-REFERENCE TO RELATED APPLICATIONS

This application claims the benefit of priority from U.S. Provisional Application No. 62/977,889, filed on Feb. 18, 2020, which is incorporated by reference herein in its entirety.

TECHNICAL FIELD

The present disclosure relates generally to endoscopic medical devices and related methods of use. More particularly, in some embodiments, the disclosure relates to one or more accessory devices used to help target sites and/or for advancing medical devices to the target sites.

BACKGROUND

Medical tools for accessing target sites within a body may be advanced through one or more lumens of an endoscope, and may extend from a distal end thereof to manipulate the target site. Drawbacks of these endoscopic systems include, for example, limited accessibility and maneuverability of tools at protruding from the distal end of the endoscope. For example, in many endoscopes, medical tools extend from one or more openings in a distal end face of the endoscope, limiting the access and maneuverability of these medical tools in a direction perpendicular to the distal end face. This creates difficulties in cutting and removing tissue from the target sites, or performing other therapies. The present disclosure may solve one or more of these problems or other problems in the art. The scope of the disclosure, however, is defined by the attached claims and not the ability to solve a specific problem.

SUMMARY OF THE DISCLOSURE

According to an aspect, an accessory device for an endoscope comprises a cap configured to be attached to a shaft of the endoscope, the cap extending along a first axis, a first tip coupled to the cap and movable relative to the cap between a deployed configuration and a non-deployed configuration, and a first shaft defining a lumen and extending proximally from the first tip, wherein, in the deployed configuration, the first tip extends along a second axis that is offset from the first axis, and in the non-deployed configuration, the first tip extends along a third axis that is offset from the first axis.

The accessory device may further include an expandable guide member, wherein the tip may be coupled to the cap via the expandable guide member.

The expandable guide member may be expanded while the tip is in the deployed configuration, and collapsed while the tip is in the non-deployed configuration.

The expandable guide member may include a first arm coupled to the cap, a hinge coupled to the first arm, and a second arm coupled to the first arm by the hinge.

An angle formed between the first axis and the second axis may be greater than 0 degrees and less than or equal to 180 degrees.

The first axis may be substantially perpendicular to the second axis.

The first tip may face radially inward in the deployed configuration.

The accessory device may further include a second tip and a second shaft defining a lumen and extending proximally from the second tip, wherein the first tip and the second tip may be located on radially opposing sides of the cap in the non-deployed configuration.

The first tip and the second tip may face toward the first axis when in the deployed configuration.

The accessory device may further comprise at least one actuation wire extending proximally from the first tip.

The accessory device may further comprise a lever rotatably attached to a proximal end of the endoscope and may be configured to move the at least one actuation wire proximally and distally.

The first tip may be configured to face different directions based on a position of the actuation wire relative to the endoscope.

The accessory device may further comprise a proximal mounting clip configured to mount the accessory device to a handle of the endoscope.

The accessory device may further comprise at least one intermediate mounting clip disposed between the proximal mounting clip and the cap, wherein the at least one intermediate mounting clip may include a shaft opening configured to receive the first shaft.

The accessory device may further comprise an attachment device configured to attach the first tip to the cap when the tip is in the non-deployed configuration, wherein the attachment device may include one or more of a magnet, a clip, or an adhesive.

According to another aspect, an accessory device for an endoscope comprises a cap including a body and two distal tips, each of the two distal tips having a deployed configuration and a non-deployed configuration, wherein the two distal tips are diametrically opposed on the body, and each of the two distal tips is hingedly attached to the cap, and a first shaft and a second shaft, each of the first shaft and the second shaft defining a lumen and extending to the cap, wherein a distal end of the first shaft is connected to a first distal tip of the two distal tips and a distal end of the second shaft is connected to a second distal tip of the two distal tips, wherein the first distal tip and the second distal tip are each configured to move distally of the distal end cap when in the deployed configuration.

The accessory device may further comprise a pair of expandable guide members, wherein each of the expandable guide members may include a first arm and a second arm, wherein a first end of the first arms may be pivotally attached to a respective distal tip of the two distal tips, a first end of the second arms may be pivotally attached to the cap, and a second end of the first arms may be hingedly attached to a second end of the respective second arms.

According to yet another aspect, a method comprises attaching an accessory device to an endoscope, wherein the accessory device includes a proximal mounting clip, a distal end cap, and at least one accessory shaft extending between the proximal mounting clip and the distal end cap, and wherein the endoscope includes a handle and a shaft extending in a distal direction from the handle, inserting the endoscope and the accessory device into a body to opening, advancing the endoscope so that the distal end cap is adjacent to a target site, wherein a distal face of the endoscope extends along a longitudinal axis while the distal end cap is adjacent to the target site, deploying at least one distal end tip of the distal end cap so that the distal end cap extends along an axis that is offset from the longitudinal axis, and advancing a medical instrument through the accessory shaft, and out of an opening at the distal end of the at least one distal end tip.

The method may further comprise advancing an actuation wire in a distal direction to deploy the at least one distal end tip from a non-deployed configuration to a deployed configuration.

The method may further comprise moving the actuation wire in the distal direction or a proximal direction to change an orientation of a distal end face of the at least one distal end tip relative to the longitudinal axis.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
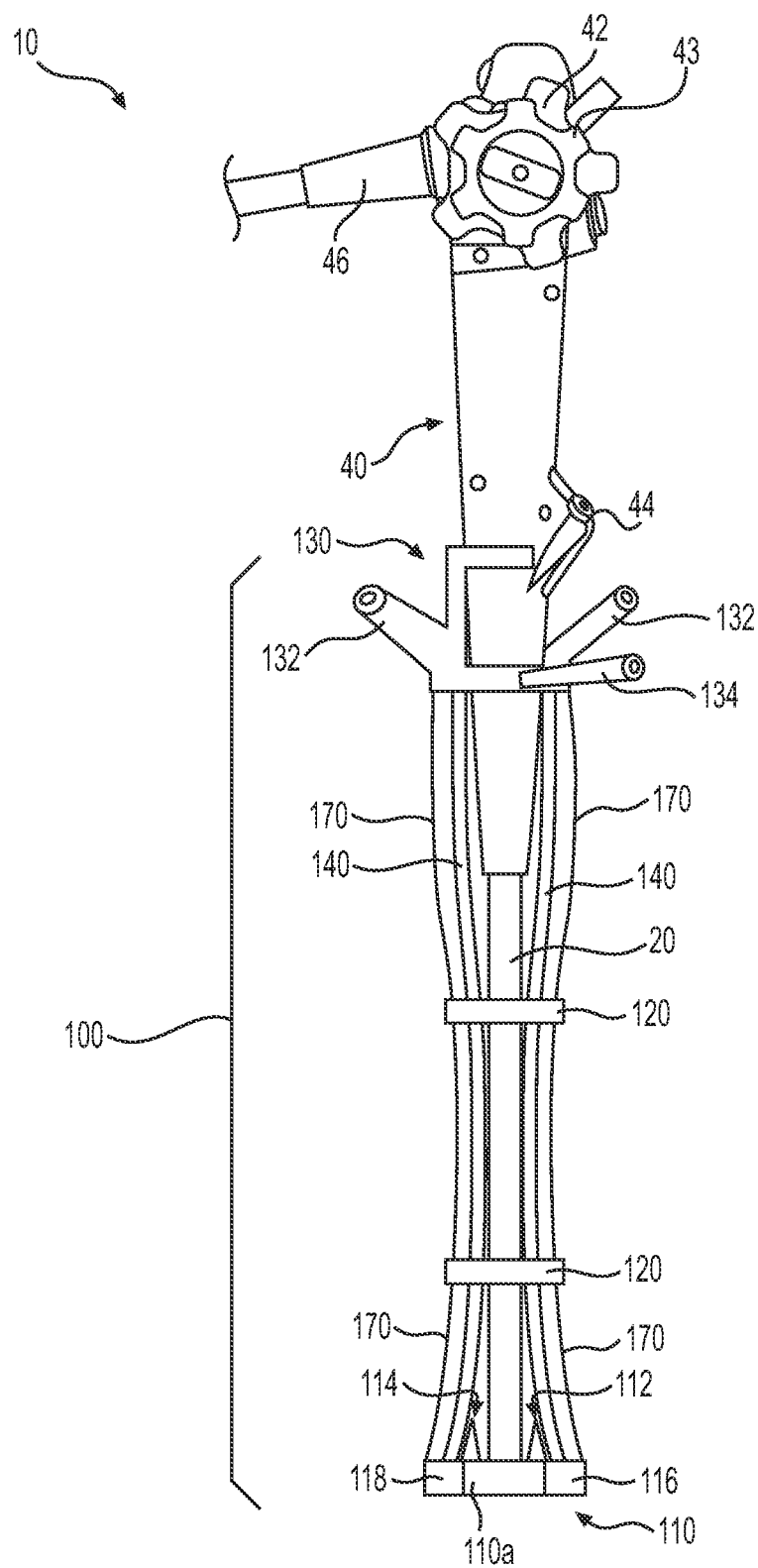
FIG. 1 is a schematic view of a medical system according to an embodiment.

The present disclosure is described with reference to exemplary medical systems and medical tools for accessing a target site, for example, for accessing a target site from different directions and/or different angles at a distal end of an endoscope. This may provide improved medical tool functionality and/or assist medical professionals to gain improved access to the target site for performing medical procedures. However, it should be noted that reference to any particular device and/or any particular procedure is provided only for convenience and not intended to limit the disclosure. A person of ordinary skill in the art would recognize that the concepts underlying the disclosed devices and application methods may be utilized in any suitable procedure, medical or otherwise. The present disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/−10% of a stated or implied value.

Additionally, terms that indicate the geometric shape of a component/surface refer to exact and approximate shapes.

Referring to FIG. 1, a medical system 10 according to an embodiment is shown. Medical system 10 includes a shaft 20 (e.g., a catheter) and a handle 40 connected at a proximal end of shaft 20. Shaft 20 may be flexible, but the rigidity/flexibility of shaft 20 is not limited. Shaft 20 may be an endoscope, a colonoscope, a bronchoscope, a ureteroscope, or other like-device (not shown). Handle 40, or some other device for actuating or controlling medical system 10 and any tools or devices associated with medical system 10, includes first and second actuating devices 42, 43. Devices 42, 43 control articulation of shaft 20, and/or an articulation joint at a distal end of shaft 20, in multiple directions. Devices 42, 43, may be, for example, rotatable knobs that rotate about their axes to push/pull actuating elements (not shown). The actuating elements, such as cables or wires suitable for medical procedures (e.g., medical grade plastic or metal), extend distally from a proximal end of medical system 10 and connect to shaft 20 to control movement thereof. Alternatively, or additionally, a user may operate actuating elements independently of handle 40. Distal ends of actuating elements extend through shaft 20 and terminate at an actuating joint and/or a distal tip of shaft 20. For example, one or more actuating elements may be connected to an articulation joint, and actuation of actuating elements may control the actuating joint or the distal end of shaft 20 to move in multiple directions.

Figure 5:
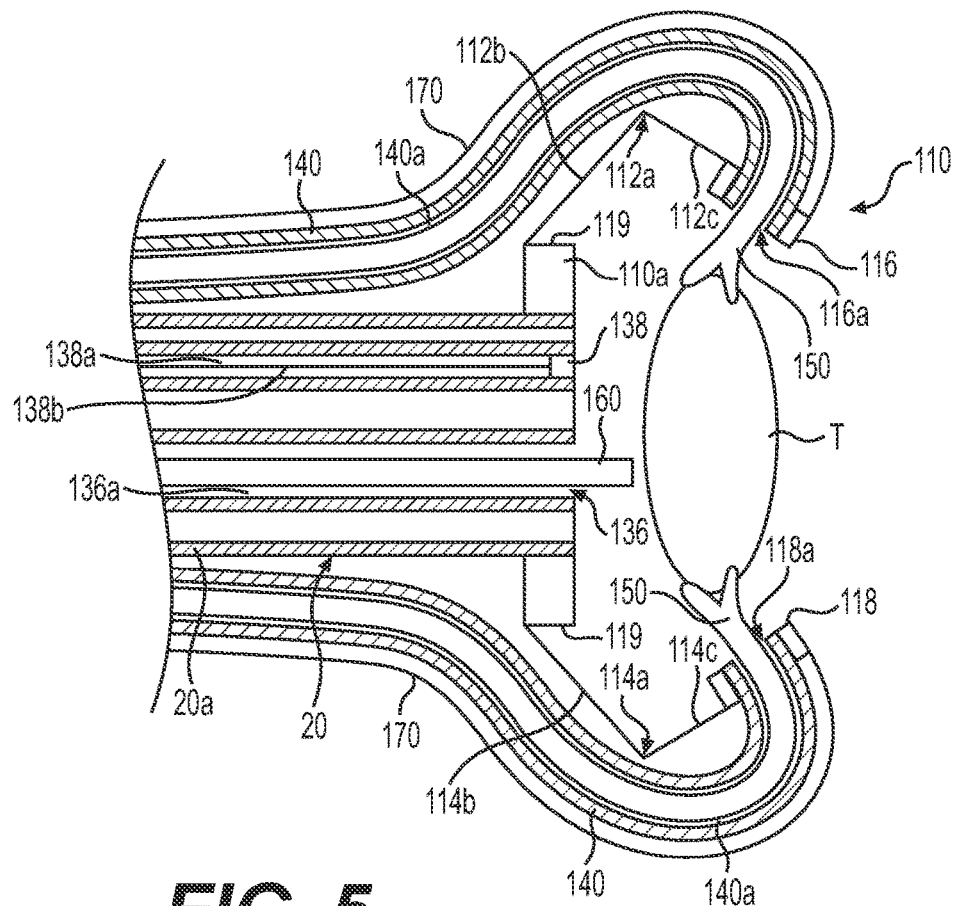
FIG. 5 is a cross-section of the medical system of FIG. 1 in a deployed configuration, according to an embodiment.

One or more electrical cables (such as the electrical cable 138b disposed in a light lumen 138a, shown in FIG. 5) may extend from the proximal end of shaft 20 to the distal end of shaft 20. Cables (e.g., cable 138b) may provide electrical controls to imaging, lighting, and/or other electrical devices 138 (shown in FIG. 5) at the distal end of shaft 20, and may carry imaging signals from the distal end of shaft 20 proximally to be processed and/or displayed on a display. Handle 40 may also include ports 44, 46 for introducing and/or removing tools, fluids, or other materials from the patient. Port 44 may be used to introduce tools. Port 46 may be connected to an umbilicus for introducing fluid, suction, and/or wiring for electronic components. For example, as shown in FIG. 1, port 44 may be connected to a lumen (such as working channel 136a shown in FIG. 5), which extends from the proximal end to the distal end of shaft 20. Port 44 may receive a medical device, such as medical device 160 (e.g., an ablation device), as shown in FIG. 5.

According to an example, FIG. 1 shows a device 100 (e.g., an accessory device) may be attachable to shaft 20 and/or handle 40. Device 100 may include a distal end cap 110, which may be attachable to a distal end of shaft 20. Distal end cap 110 may be attached to a distalmost end of shaft 20, or distal end cap 110 may be disposed proximally to the distalmost end of shaft 20. Device 100 may also include one or more mounting clips 120 provided between distal end cap 110 and a proximal mounting clip 130. One or more sheaths 140 may extend from a proximal (e.g., a proximalmost) mounting clip 130 to distal end cap 110, and may be supported along a length of shaft 20 by one or more mounting clips 120. Sheaths 140 may be flexible, but the rigidity/flexibility is not limited. While distal end cap 110 is shown having an oval shape, the shape of distal end cap 110 is not limited thereto, and may be circular, rectangular, or any other shape.

Proximal mounting clip 130 may be attached to handle 40 (e.g., a distal end of handle 40) via snap fit, a clip with or without a set screw, an adhesive, welding, hook-and-loop fastener (e.g., Velcro), or the like. While device 100 may be removably attached to medical system 10, device 100 may also be permanently or fixedly attached to medical system 10, e.g., device 100 may not be removed without destroying medical system 10. The location and attachment means of proximal mounting clip 130 to handle 40 is not limited, and may be changed to correspond to the shape of handle 40. Proximal mounting clip 130 may include one or more ports 132, each of which may be coupled to a lumen of respective sheaths 140. Ports 132 may receive medical devices, e.g., medical instruments having end effectors such as graspers, baskets, scissors, or the like, and the medical devices may be advanced along (through) the lumen of respective sheaths 140 to distal openings in distal end cap 110, as will be described herein. Proximal mounting clip 130 may also include an actuation device 134 (e.g., a lever) for actuating one or more wires 170, where wires 170 extend from proximal mounting clip 130 to distal end cap 110. As will be described herein, wires 170 may cause distal ends of sheaths 140 to move relative to distal end cap 110 and/or shaft 20. While actuation device 134 is disposed on proximal mounting clip 130, the location is not limited thereto, and the position may be selected according to ergonomic and/or functional requirements.

Figure 2A:
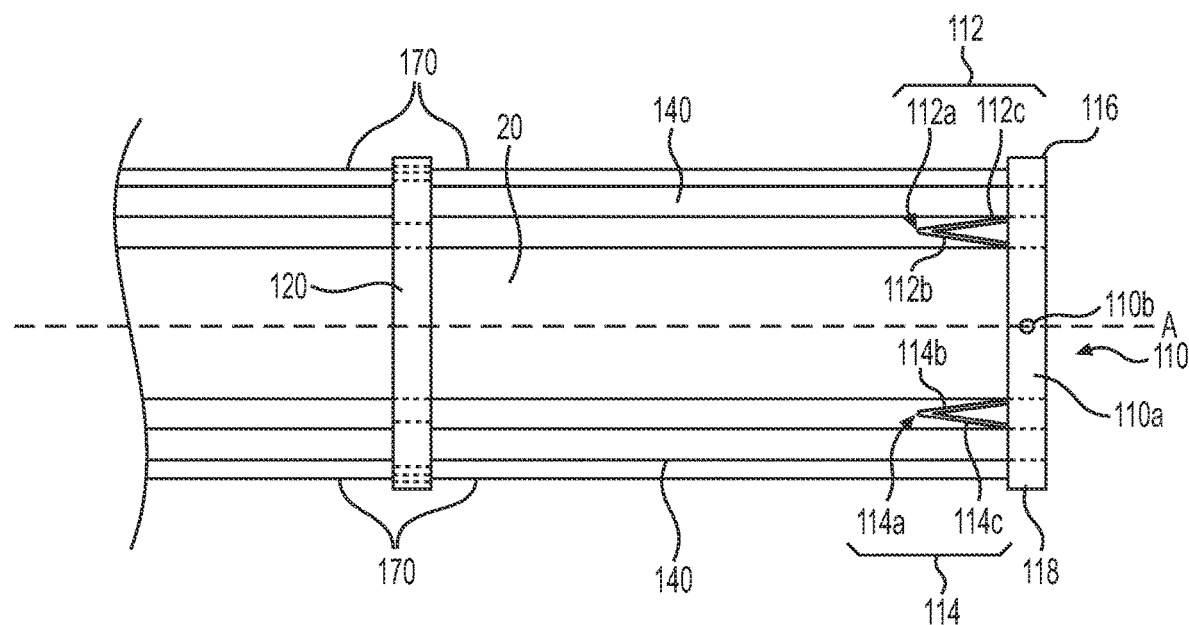
FIGS. 2A-2C are views of a distal end of the medical system of FIG. 1 in a non-deployed configuration, according to an embodiment.

With reference to FIGS. 1 and 2A, distal end cap 110 includes two guide members 112, 114 (although other suitable numbers of guide members, e.g., one, three, four, or more, are also contemplated). Each guide member 112, 114 is connected together by a respective hinge 112a, 114a (see FIG. 2A). Guide member 112 includes a first arm 112b, a second arm 112c, and hinge 112a connecting first arm 112b to second arm 112c. An end of first arm 112b opposite hinge 112a is attached to a body 110a of distal end cap 110. An end of second arm 112c opposite hinge 112a is attached to a first distal tip 116. Guide member 114 have a similar arrangement, with a first arm 114b attached to body 110a of distal end cap 110, a second arm 114c attached to a second distal tip 118, and hinge 114a connecting first and second arms 114b, 114c.

First and second distal tips 116, 118 may be actuated via wires 170. Wires 170 may extend from the proximal end of shaft 20 to the distal end. For example, wires 170 may be attached at distal ends of first and second distal tips 116, 118 as shown in FIGS. 2A and 2C, and to lever 134. Alternatively, wires may be attached to any portion of guide members 112, 114, including but not limited to hinges 112a, 114a. Movement of lever 134 may move one or both of wires 170 in a proximal direction or a distal direction. Alternatively, wires 170 may be independently actuated by, e.g., separate levers or actuators, or by different states of the same levers or actuators. Wires 170 may have sufficient stiffness to receive a force to move wires 170 in a distal direction to overcome a force maintaining first and second distal tips 116, 118 in a non-deployed configuration, as will be described herein. Wires 170 may include a single filament having a sufficient diameter and rigidity, may be a coil or bundle of filaments, or the like. In addition, wires 170 may be moved in a proximal direction to move first and second distal tips 116, 118 from a deployed configuration (e.g., FIG. 3A) to the non-deployed configuration (e.g., FIG. 2A). As discussed herein, wires 170 may pass through holes 124 in mounting clips 120 (see FIG. 4A) which may assist in guiding wires 170 and/or to provide additional support. However, wires 170 may extend adjacent shaft 20 from the proximal end to the distal end without passing through holes 124 in mounting clips 120.

Figure 2B:
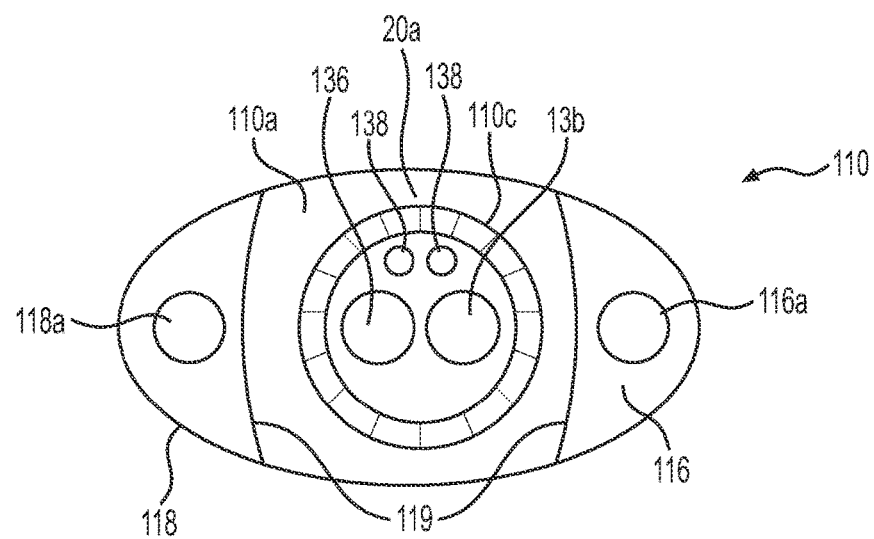
Figure 2C:
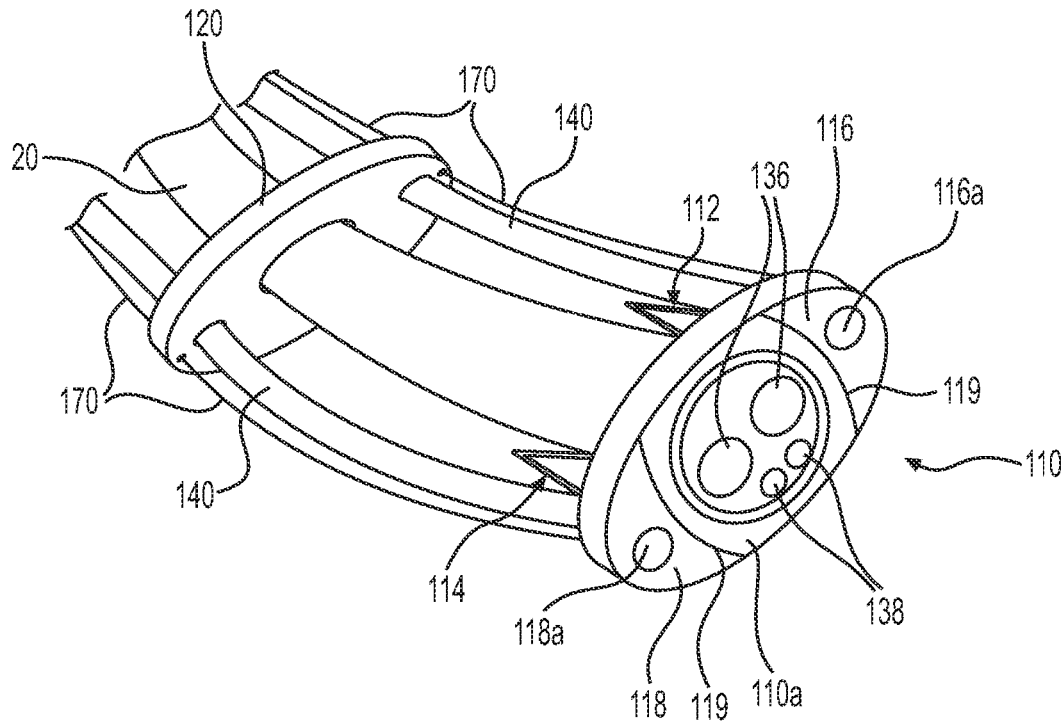

FIGS. 2B and 2C further illustrate distal end cap 110 in a non-deployed configuration, in which first distal tip 116 and second distal tip 118 are each attached to lateral sides of body 110a of distal end cap 110 at separation joints 119 via, e.g., a magnet, a snap-fit, an adhesive, or the like. It will be understood that tabs or other connectors (not shown) on first and second distal tips 116, 118 may contact a distal and/or a proximal side of body 110a to assist in attaching first distal tip 116 and second distal tip 118 to body 110a. Alternatively, or additionally, first distal tip 116 and second distal tip 118 may rest against respective lateral side of body 110a, e.g., biased there by guide members 112, 114.

A force on wires 170 in the proximal direction (or the release of the distally-directed force) may move first distal tip 116 and second distal tip 118 into the non-deployed configuration. For example, activating actuation device 134 when first distal tip 116 and second distal tip 118 are in the deployed configuration may cause wires 170 to pull first distal tip 116 and second distal tip 118 in the proximal direction. Pulling wires 170 in the proximal direction may overcome a biasing force of guide members 112, 114, thereby moving first distal tip 116 and second distal tip 118 in the proximal direction to rest against separation joints 119 in the non-deployed configuration.

In the non-deployed configuration, distal end faces of first distal tip 116 and second distal tip 118 are disposed in a first orientation, e.g., with the distal end faces approximately perpendicular to a longitudinal axis A, as shown FIG. 2A. The first orientation is not limited to this example. For example, the distal end faces of first distal tip 116 and second distal tip 118 may form angles with longitudinal axis A, as described below. Activation of guide members 112, 114 may change the orientation of distal end faces of first distal tip 116 and/or second distal tip 118 relative to longitudinal axis A. For example, activation of guide members 112, 114 may cause first distal tip 116 and/or second distal tip 118 to move distally of distal end cap 110, may change the orientation of first distal tip 116 and/or second distal tip 118 relative to longitudinal axis A, etc.

Figure 6:
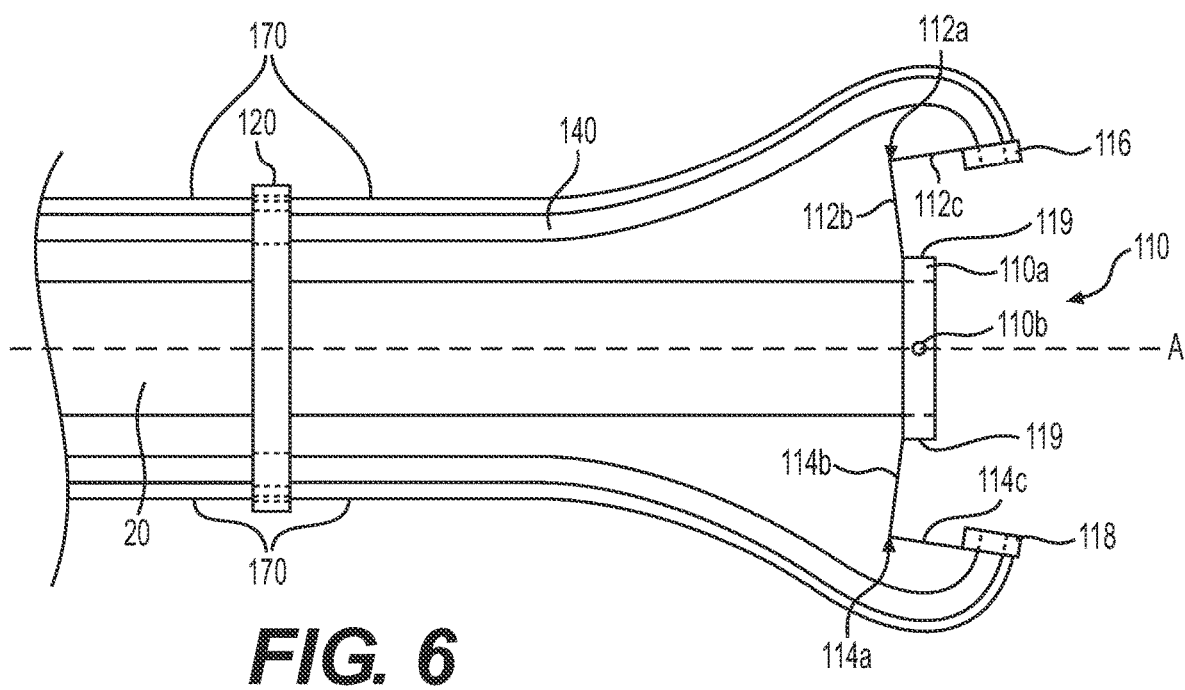
FIG. 6 is a side view of the medical system of FIG. 1 in a deployed configuration, according to an embodiment.

A distal end face of each of first distal tip 116 and second distal tip 118 may include at least one opening 116a, 118a, respectively, that connect to a respective lumen of a sheath 140. It will be understood that each first distal tip 116 and second distal tip 118 may include additional openings such that multiple medical instruments may be deployed through the openings, as will be described herein. Body 110a of distal end cap 110 includes a central lumen 110c to receive shaft 20. An outer diameter of a shaft outer wall 20a (FIG. 5) of shaft 20 may be smaller than or approximately a same size as a diameter of central lumen 110c, thereby providing a friction attachment between body 110a of distal end cap 110 a shaft 20. Alternatively, or additionally, a set screw may be inserted into hole 110b (see FIGS. 2A, 3A, and 6) to provide additional support for securing distal end cap 110 to shaft 20.

With continued reference to FIGS. 2B and 2C, shaft 20 may include multiple lumens. These lumens may include lumens for light emitting elements (e.g., light lumens 138a, shown in FIG. 5) which terminate at openings and/or imaging or lighting devices 138. Shaft 20 may also include working channels (e.g., working channels 136a, shown in FIG. 5) which may receive medical instruments, and which may terminate at openings 136. Medical instruments may extend from a proximal end of working channels 136a, and the medical instruments may extend from opening 136 in a distal end of shaft 20 such that the medical professional may perform a therapy, e.g., cutting, grasping, or other therapies on a target tissue T (see FIG. 5). The medical professional may control the medical instruments and/or the light emitting elements at a proximal end of shaft 20 via, e.g., switches, knobs, or other control mechanisms on or associated with handle 40.

Figure 3A:
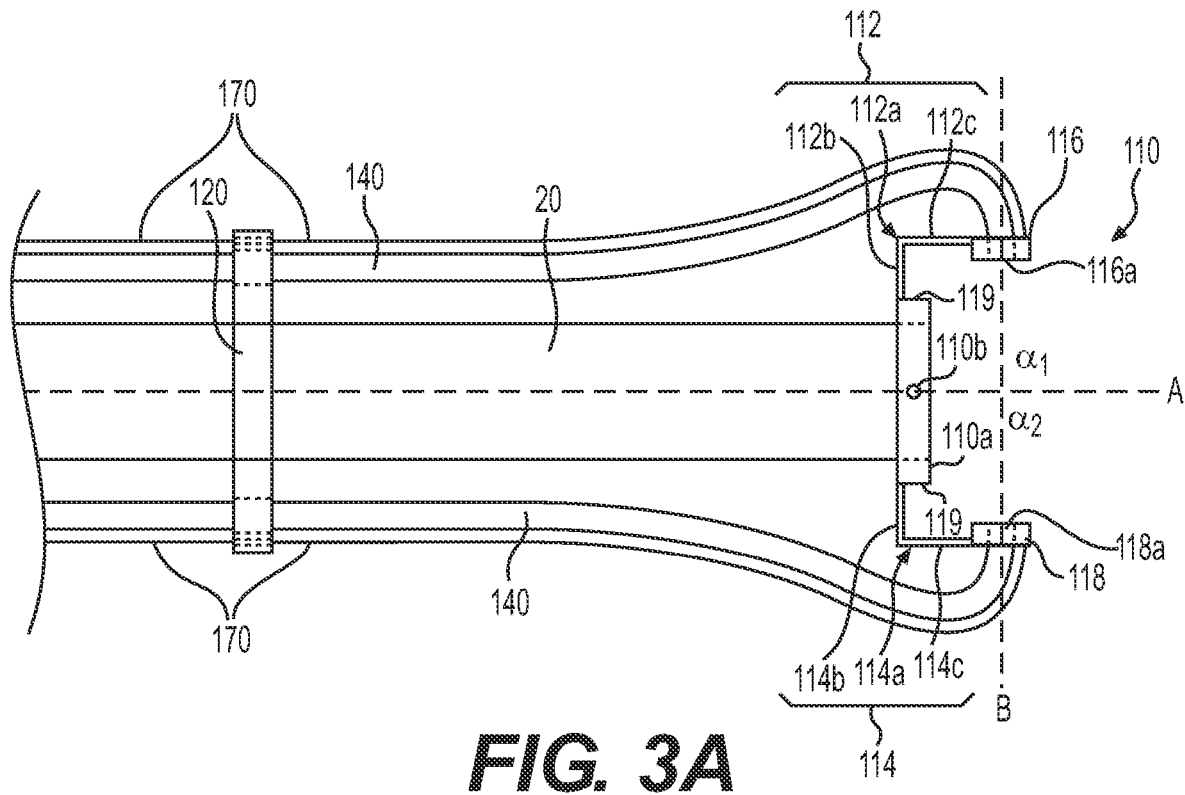
FIGS. 3A and 3B are views of the distal end of the medical system of FIG. 1 in a deployed configuration, according to an embodiment.
Figure 3B:
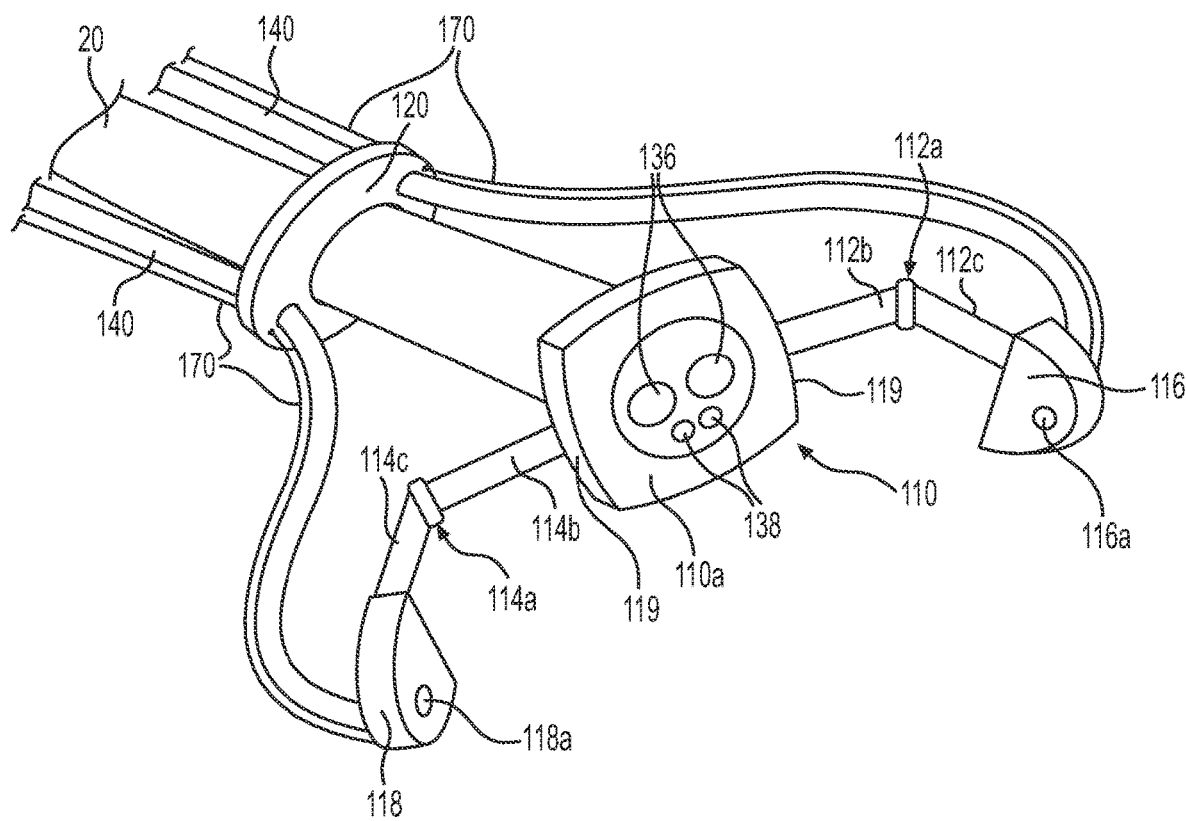

FIGS. 3A and 3B illustrate a deployed configuration of distal end cap 110 according to an example. Hinges 112a, 114a may include a spring or other biasing mechanism such that once first and second distal tips 116, 118 are deployed, first arm 112b and second arm 112c may form approximately up to a 90 degree angle therebetween, and first arm 114b and second arm 114c may also form approximately up to a 90 degree angle therebetween. In this manner, the medical personnel may access a target site from a direction approximately perpendicular to openings 136, which may allow the medical personnel to pull or cut tissue in a direction substantially perpendicular to openings 136 and any instruments extending from openings 136. Alternatively, the angle between the arms of guide members 112, 114 may be selected based on the position of wires 170. For example, wires 170 may be actuated such that the angle between the arms of guide members 112, 114 may be changed throughout a procedure to allow the medical professional to access a target site from different angles.

In addition, the hinged connection between first arm 112b to body 110a and the hinged connection between second arm 112c and first distal tip 116 may orient first distal tip 116 such that opening 116a is offset, e.g., substantially parallel, to a longitudinal axis A of shaft 20. The hinged connection between first arm 114b and body 110a and the hinged connection between second arm 114c and second distal tip 118 may similarly allow opening 118a to be offset from longitudinal axis A when in the deployed configuration at a same or a different offset as opening 116a. As will be described herein, the angle between first and second arms 112b, 112c and first and second arms 114b, 114c is not limited to 90 degrees. Further, wires 170 may maneuver first and second distal tips 116, 118 to orient openings 116a, 118a at different angles relative to longitudinal axis A.

A longitudinal axis B extends through each of openings 116a and 118a. Angles are formed between longitudinal axis A and longitudinal axis B. For example, a first angle α1 is formed between longitudinal axis A and longitudinal axis B extending from opening 116a. A second angle α2 is formed between longitudinal axis A and longitudinal axis B extending from opening 118a. An angle of α1 and an angle of α2 may be greater than 0 degrees and less than or equal to 180 degrees. For example, when the angle of al is between 0 degrees and 90 degrees, openings 116a faces a distal direction. When the angle of al is 90 degrees, opening 116a is parallel to longitudinal axis A. When the angle of al is between 90 degrees and 180 degrees, distal opening 116a faces a proximal direction, and when the angle of α1 is 180 degrees, opening 116a faces the distal end face of distal end cap 110 (i.e., faces proximally) and is offset to longitudinal axis A. Opening 118a may be similarly oriented based on similar angles of α2.

Figure 4A:
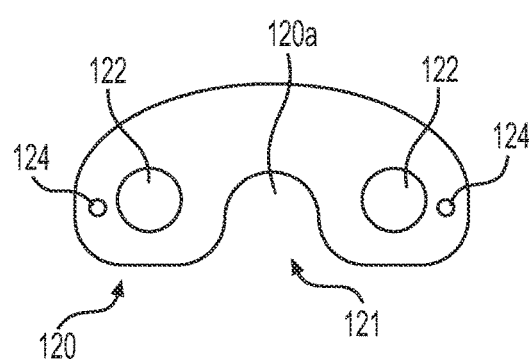
FIG. 4A is a front view of a mounting clip of the medical system of FIG. 1, according to an embodiment.
Figure 4B:
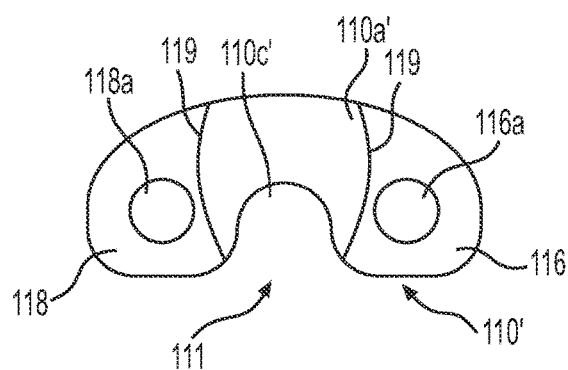
FIG. 4B is a front view of a distal end cap of the medical system of FIG. 1, according to an embodiment.

FIGS. 4A and 4B show an example of mounting clip 120 and a distal end cap 110', respectively. Distal end cap 110' illustrates a modified shape and connection means from distal end cap 110. Mounting clip 120 and distal end cap 110' may snap onto shaft 20 via respective openings 121, 111. For example, mounting clip 120 and distal end cap 110' may have a C-shape configuration, and respective openings 121, 111 may have a diameter less than the diameter of the outermost surface of shaft 20. Mounting clip 120 and distal end cap 110' may then be attached to shaft 20 by pushing each mounting clip 120 and distal end cap 110' onto shaft 20 at the appropriate locations along a length of shaft 20, such that shaft 20 is received by a central recess 120a of mounting clip 120 and by a central recess 110c' formed in a body 110a' of distal end cap 110'. The snap-fit configuration may be used alternatively to, or in addition to, a set screw in hole 110b of distal end cap 110 (FIGS. 2A and 3A). First and second distal tips 116, 118 may be arranged on body 110a' in a similar manner, and may be deployed in a similar manner, as described relative to distal end cap 110.

Mounting clip 120 in FIG. 4A may include a pair of first openings 122 and second openings 124. First openings 122 may be diametrically opposed on either side of central lumen 120 (first openings 122 are not limited to being diametrically opposed on either side of central lumen 120). Second openings 124 may also be diametrically opposed on either side of central lumen 120 (second openings 124 are not limited to being diametrically opposed on either side of central lumen 120), and may be positioned radially inward (as shown in FIG. 4A) or radially outward from first openings 124. First openings 122 may receive sheaths 140 and may support sheaths 140 along a length of shaft 20 when mounting clips 120 are connected thereto. Second openings 124 may receive wires 170 and may similarly support wires 170. First and second openings 122, 124 may have inner diameters greater than an outer diameter of sheath 140 and wires 170, respectively. This may allow sheaths 140 and wires 170 to move proximally and distally with respect to shaft 20, as will be described herein.

A cross-section of the distal end of device 100 is shown in FIG. 5, in which distal end cap 110 is in a deployed configuration. Medical instruments 150 may extend through lumens 140a of sheaths 140 from a proximal end of sheaths 140 (e.g., adjacent handle 40) and protrude from openings 116a, 118a in first distal tip 116 and second distal tip 118, respectively. Medical instruments 150 may include grasping elements at a distal end, but are not limited thereto. Medical instruments 150 may include any end effector including, but not limited to, a knife, a net, an ablation device, a stapler, or the like.

As described herein, a second medical instrument 160, such as an ablation device, may extend through working channel 136a from a proximal end of shaft 20 (e.g., adjacent handle 40) and protrude from opening 136 at a distal end of shaft 20. Second medical instrument 160 is also not limited to an ablation device, and may include any end effector, such as but not limited to grasping elements, a knife, a net, a stapler, or the like. Light emitting elements and/or imaging elements may be disposed at distal end 138 of light lumen 138a and may provide visualization of target site T. Electricity and/or image data may travel along cable 138b disposed in light lumen 134a from the distal end of shaft 20 to the proximal end of shaft 20. Cable 138b may be connected to a power supply and/or m be connected to a visualization device, such as a monitor or the like.

A method of operating medical system 10 will now be described. Device 100 may be attached to endoscope 20 and handle 40 via proximal mounting clip 130, mounting clips 120, and distal end cap 110. For example, proximal mounting clip 130 may be attached to any portion of handle 40 by snap-fit, an adhesive, a tether, one or more set screws, or the like. Mounting clip 120 and distal end cap 110 may be similarly attached to shaft 20 by snap-fit, an adhesive, a tether, one or more set screws, or the like.

Shaft 20 may be inserted into a body via a natural orifice, an incision, or any other opening in the body and advanced to target site T. A medical professional may visualize the distal end of shaft 20 using one or more light emitting elements at distal end 138 of light lumen 138a and/or a visualization device (e.g., a camera or other image sensor) at or extending through one or more openings 136. Medical instruments may be introduced to one or more working channels 136a via ports 44, 46. Medical instruments and/or visualization devices may also be introduced to lumens 140a of sheath 140 via ports 132. The medical instruments and/or visualization devices may extend from openings 116a, 118a, 138 to perform medical procedures and/or provide visualization of target site T. It will be understood that medical instruments and/or visualization devices may be introduced into respective lumens at any time during the medical procedure.

After positioning the distal end of shaft 20 at target site T, first and second distal tips 116, 118 may be deployed. For example, the medical professional may actuate first and second distal tips 116, 118 by pushing distally on wires 170 to overcome a holding force acting on to each of first and second distal tips 116, 118 at separation joints 119 so that distal end faces of first distal tip 116 and second distal tip 118 are offset from longitudinal axis A. After the holding force is overcome, first and second distal tips 116, 118 are deployed, where each of arms 112b, 112c and arms 114b, 114c form angles of approximately 90 degrees. Deployment of first and second distal tips 116, 118 causes first and second distal tips 116, 118 to move distally of the distalmost end of shaft 20. Medical instruments and/or visualization devices may then be extended from openings 116a, 118a to provide additional visualization and/or to allow the medical professional to perform cutting, grasping, stapling, or the like of target site T. Additionally, guide members 112, 114 may allow additional angles of movement, such that the medical professional may push wires 170 distally and/or pull wires 170 proximally to change an orientation of first and second distal tips 116, 118 relative to longitudinal axis A.

After completion of the medical procedure, the medical professional may move wires 170 proximally until the attachment mechanism at separation joints 119 attaches first and second distal tips 116, 118 in the non-deployed configuration. Subsequently, the medical professional may withdraw the medical instruments and/or the visualization devices into working channels 136a and/or lumens 140a. Shaft 20 may then be moved proximally to remove shaft 20 from the body. It will be understood that the medical instruments and/or the visualization devices may be introduced to working channels 132a and/or lumens 140a at any point during the medical procedure. Further, the medical instruments may be extended from respective openings 116a, 118a, and 136 at any time during the procedure to access target site T.

While different medical systems have been described, it will be understood that the particular arrangements of elements in these medical systems are not limited. Moreover, a size and a shape of the catheter or shaft of the medical system, or the medical instruments used with the medical system, and/or the method of deploying the system, are not limited. As described in examples herein, distal tips may be extended distally of a distalmost end of the shaft, allowing for improved visualization and/or access to a target site. For example, in certain procedures, accessing the target site from multiple different directions may improve the results of the medical procedure, may decrease the time of the medical procedure, and may improve recovery times of the patient after the medical procedure.

It will be apparent to those skilled in the art that various modifications and variations can be made to the disclosed device without departing from the scope of the disclosure. For example, the angle of each of the pairs of arms and/or the angle of the openings of the distal tips relative to the longitudinal axis may be modified based on a desired medical therapy. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An accessory device for an endoscope, the accessory device comprising:
    a cap configured to be attached to a shaft of the endoscope, the cap extending along a first axis;
    an expandable guide member including:
        a first arm having a first end coupled to the cap; and
        a second arm having a first end coupled to a second end of the first arm;
    a first tip coupled to a second end of the second arm and movable relative to the cap between a deployed configuration and a non-deployed configuration;
    a first shaft defining a lumen and extending proximally from the first tip,
    a second tip and a second shaft defining a lumen and extending proximally from the second tip; and
    a releasable attachment device configured to attach the first tip to the cap when the first tip is in the non-deployed configuration and to permit the first tip to release from the cap to transition the first tip from the non-deployed configuration to the deployed configuration;
    wherein, in the deployed configuration, the first tip extends along a second axis that is offset from the first axis, and in the non-deployed configuration, the first tip extends along a third axis that is offset from the first axis; and
    wherein the first tip and the second tip are located on radially opposing sides of the cap in the non-deployed configuration.

2. The accessory device of claim 1, wherein the expandable guide member is expanded while the first tip is in the deployed configuration, and collapsed while the first tip is in the non-deployed configuration.

3. The accessory device of claim 1, wherein the expandable guide member further includes a hinge coupled to the second end of the first arm, and wherein the first end of the second arm is coupled to the second end of the first arm by the hinge.

4. The accessory device of claim 1, wherein an angle formed between the first axis and the second axis is greater than 0 degrees and less than or equal to 180 degrees, and wherein the first axis is substantially perpendicular to the second axis.

5. The accessory device of claim 1, wherein the first tip faces radially inward in the deployed configuration.

6. The accessory device of claim 1, wherein the first tip and the second tip face toward the first axis when in the deployed configuration.

7. The accessory device of claim 1, further comprising at least one actuation wire extending proximally from the first tip, and further comprising a lever rotatably attached to a proximal end of the endoscope and configured to move the at least one actuation wire proximally and distally.

8. The accessory device of claim 7, wherein the first tip is configured to face different directions based on a position of the at least one actuation wire relative to the endoscope.

9. The accessory device of claim 1, wherein the releasable attachment device includes one or more of a magnet, a clip, or an adhesive.

10. The accessory device of claim 1, wherein the first tip moves distally of the cap in the deployed configuration from a position not distal to the cap in the non-deployed configuration.

11. An accessory device for an endoscope, the accessory device comprising:
 a proximal mounting clip configured to mount the accessory device to a handle of the endoscope;
 a cap including a body and two distal tips, each of the two distal tips having a deployed configuration and a non-deployed configuration, wherein the two distal tips are diametrically opposed on the body, and each of the two distal tips is hingedly attached to the cap;
 for each of the two distal tips, a first arm and a second arm hingedly coupled to each other for attaching each of the two distal tips to the cap, wherein a first interior hinge angle formed between the first arm and the second arm when a respective distal tip of the two distal tips is in the non-deployed configuration is smaller than a second interior hinge angle formed between the first arm and the second arm when the respective distal tip of the two distal tips is in the deployed configuration; and
 a first shaft and a second shaft, each of the first shaft and the second shaft defining a lumen and extending to the cap, wherein a distal end of the first shaft is connected to a first distal tip of the two distal tips and a distal end of the second shaft is connected to a second distal tip of the two distal tips,
 wherein the first distal tip and the second distal tip are each configured to move distally of the cap when in the deployed configuration from a position not distal to the cap in the non-deployed configuration.

12. The accessory device of claim 11, further comprising at least one intermediate mounting clip disposed between the proximal mounting clip and the cap, wherein the at least one intermediate mounting clip includes a shaft opening configured to receive the first shaft.

13. The accessory device of claim 11, wherein the first arm and the second arm for each of the two distal tips comprise an expandable guide member, wherein a first end of the first arm is pivotally attached to a respective distal tip of the two distal tips, a first end of the second arm is pivotally attached to the cap, and a second end of the first arm is hingedly attached to a second end of the second arm.

14. The accessory device of claim 11, wherein the body of the cap includes a central opening to receive a shaft of the endoscope.

15. The accessory device of claim 11, further comprising a first releasable attachment device and a second releasable attachment device each configured to respectively attach the first tip and the second tip to the cap when each of the first tip and the second tip is in the non-deployed configuration to permit each of the first tip and the second tip to release from the cap to transition each of the first tip and the second tip from the non-deployed configuration to the deployed configuration.

16. A method, comprising:
 attaching an accessory device to an endoscope, wherein the accessory device includes a proximal mounting clip having one or more ports, a distal end cap, two distal tips coupled to the distal end cap, a first accessory shaft extending between the proximal mounting clip and a first tip of the two distal tips, and a second accessory shaft extending between the proximal mounting clip and a second tip of the two distal tips, wherein the first tip and the second tip are located on radially opposing sides of the distal end cap in a non-deployed configuration, wherein the endoscope includes a handle and a shaft extending in a distal direction from the handle, and wherein the proximal mounting clip is attached to the handle;
 inserting the endoscope and the accessory device into a body opening;
 advancing the endoscope so that the distal end cap and the two distal tips are adjacent to a target site, wherein a distal face of the endoscope extends along a longitudinal axis while the distal end cap and the two distal tips are adjacent to the target site;
 moving the first tip of the two distal tips distally of the cap from a position not distal to the cap so that the first tip of the two distal tips extends along an axis that is offset from the longitudinal axis; and
 advancing a medical instrument into the one or more ports of the proximal mounting clip, through the first accessory shaft, and out of an opening at a distal end of the first tip of the two distal tips.

17. The method according to claim 16, further comprising:
 advancing an actuation wire in a distal direction to deploy the first tip of the two distal tips from a non-deployed configuration to a deployed configuration; and
 moving the actuation wire in the distal direction or a proximal direction to change an orientation of a distal end face of the first tip of the two distal tips relative to the longitudinal axis.

18. The method according to claim 16, wherein the accessory device further includes one or more actuation wires extending from the proximal mounting clip to the distal end cap, one or more actuation devices are disposed on the proximal mounting clip, and the method further comprises:
 moving the one or more actuation wires in a distal direction or a proximal direction via actuation of the one or more actuation devices.

19. The method according to claim 16, further comprising:
 deploying the second tip of the two distal tips so that the second tip of the two distal tips extends along an axis that is offset from the longitudinal axis; and
 advancing a second medical instrument into the one or more ports of the proximal mounting clip, through the second accessory shaft, and out of an opening at a distal end of the second tip of the two distal tips.

20. The method of claim 16, wherein the accessory device further comprises a first releasable attachment device and a second releasable attachment device each configured to respectively attach the first tip and the second tip to the cap when each of the first tip and the second tip is in the non-deployed configuration to permit each of the first tip and the second tip to release from the cap to transition each of the first tip and the second tip from the non-deployed configuration to the deployed configuration.

* * * * *